(12) United States Patent
Vogtmeier et al.

(10) Patent No.: US 10,806,426 B2
(45) Date of Patent: Oct. 20, 2020

(54) MOBILE X-RAY SYSTEM COMPRISING A MOBILE X-RAY DEVICE

(71) Applicant: KONINKLIJKE PHILIPS N.V., Eindhoven (NL)

(72) Inventors: Gereon Vogtmeier, Aachen (DE); Anand Kumar Dokania, Utrecht (NL); Ravindra Bhat, Eindhoven (NL); Jens Von Berg, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/322,512

(22) PCT Filed: Mar. 30, 2018

(86) PCT No.: PCT/EP2018/058313
§ 371 (c)(1),
(2) Date: Feb. 1, 2019

(87) PCT Pub. No.: WO2018/178344
PCT Pub. Date: Oct. 4, 2018

(65) Prior Publication Data
US 2020/0008773 A1    Jan. 9, 2020

(30) Foreign Application Priority Data

Mar. 30, 2017  (IN) .............................. 201741011359
Apr. 18, 2017  (EP) ..................................... 17166767

(51) Int. Cl.
*A61B 6/08*   (2006.01)
*A61B 6/00*   (2006.01)

(52) U.S. Cl.
CPC ................ *A61B 6/547* (2013.01); *A61B 6/08* (2013.01); *A61B 6/4405* (2013.01);
(Continued)

(58) Field of Classification Search
None
See application file for complete search history.

(56) References Cited

U.S. PATENT DOCUMENTS 6,282,264 B1 *  8/2001  Smith .................. A61B 6/0457
                                                      378/167
6,583,420 B1 *  6/2003  Nelson ................. A61B 6/4233
                                                      250/363.05
(Continued)

FOREIGN PATENT DOCUMENTS

EP          0872227 A1   10/1998
WO    WO2016079047 A1    5/2016
WO    WO2016210375 A1   12/2016

*Primary Examiner* — Thomas R Artman
(74) *Attorney, Agent, or Firm* — Larry Liberchuk

(57) ABSTRACT

The present invention relates to a mobile X-ray device, comprising: a housing with an X-ray source arranged therein, a sensor system comprising one or more sensors for aligning the X-ray source to an object to be scanned and/or detecting at least one extrinsic object in a predefined area in a vicinity of the X-ray beam of the X-ray source; a processor unit comprising determining the alignment of the X-ray source and the object to be scanned based on signals received from the sensor system; image acquisition for generating an X-ray image; activating a blockage signal for the mobile X-ray device based on signals received from the sensor system; and an interface for outputting the generated X-ray image and/or information; wherein image acquisition is blocked, if the sensor system signals one of the following: at least one extrinsic object is detected within the predefined area; lack of alignment between the X-ray source and the object to be scanned.

14 Claims, 3 Drawing Sheets

(52) U.S. Cl.
CPC ............ *A61B 6/4452* (2013.01); *A61B 6/588* (2013.01); *A61B 6/589* (2013.01)

(56) References Cited

U.S. PATENT DOCUMENTS

| | | | | |
|---|---|---|---|---|
| 6,693,291 | B2* | 2/2004 | Nelson | A61B 6/4233 |
| | | | | 250/363.01 |
| 6,851,851 | B2* | 2/2005 | Smith | A61B 6/0457 |
| | | | | 378/167 |
| 7,147,372 | B2* | 12/2006 | Nelson | A61B 6/4233 |
| | | | | 378/207 |
| 9,642,584 | B2* | 5/2017 | Niebler | A61B 6/4441 |
| 9,788,810 | B2* | 10/2017 | Ancar | A61B 6/487 |
| 10,314,554 | B2* | 6/2019 | Hoornaert | A61B 6/4233 |
| 2001/0019599 | A1 | 9/2001 | Guendel | |
| 2002/0080921 | A1* | 6/2002 | Smith | A61B 6/4464 |
| | | | | 378/189 |
| 2003/0205676 | A1* | 11/2003 | Nelson | G01T 1/2928 |
| | | | | 250/370.09 |
| 2003/0209672 | A1* | 11/2003 | Nelson | G01T 1/1644 |
| | | | | 250/505.1 |
| 2004/0008810 | A1* | 1/2004 | Nelson | G01T 1/1644 |
| | | | | 378/19 |
| 2004/0068171 | A1 | 4/2004 | Ruimi | |
| 2008/0198971 | A1 | 8/2008 | Schulze-Ganzlin | |
| 2010/0127859 | A1 | 5/2010 | Hohmann | |
| 2012/0201355 | A1 | 8/2012 | Butzine | |
| 2014/0314205 | A1 | 10/2014 | Carelsen | |
| 2015/0313568 | A1 | 11/2015 | Guez | |
| 2016/0374641 | A1* | 12/2016 | Ancar | A61B 6/587 |
| | | | | 378/206 |
| 2017/0071558 | A1 | 3/2017 | Hoornaert | |
| 2017/0322484 | A1* | 11/2017 | Erhard | G03B 42/026 |
| 2020/0008773 | A1* | 1/2020 | Vogtmeier | A61B 6/4452 |
| 2020/0060635 | A1* | 2/2020 | Vogtmeier | A61B 6/563 |

* cited by examiner

MOBILE X-RAY SYSTEM COMPRISING A MOBILE X-RAY DEVICE

FIELD OF THE INVENTION

The present invention relates to mobile X-ray systems and the operation thereof.

BACKGROUND OF THE INVENTION

X-ray systems are using ionizing radiation which could be extremely dangerous when a person is radiated with a high dose. This might happen if a person is in a position close to an X-ray window of an X-ray tube. Experts might know this very well and in fixed settings e.g. in a hospital means are provided to reduce the risk of unwanted radiation, e.g. X-ray shielding walls, an interlock mechanism that allows X-ray only when doors are locked, lead apron etc.

For mobile X-ray systems, such means might be less suitable, especially when using a mobile X-ray system in acute trauma cases at the point of an accident, for example. Further scenarios are ambulance cars and services for nursing homes where a mobile X-ray system is used for medical support of a patient.

SUMMARY OF THE INVENTION

There may thus be a need for a safe operation of a mobile X-ray system to avoid unwanted radiation to bystanders and/or people located too close to the X-ray source.

The object of the present invention is solved by the subject-matter of the independent claims. Further embodiments are incorporated in the dependent claims. It should be noted that the following described aspects of the invention apply for the mobile X-ray device, the mobile X-ray system as well as for the described method for image acquisition by use of the mobile X-ray system and vice versa.

Mobile X-ray systems might become an attractive solution for rural areas but also for areas with high population density when additional diagnostic imaging is required Mobile X-ray systems not necessarily use infrastructure for sensing as in known stationary systems.

In a scenario where less trained or less instructed people are operating a mobile X-ray device outside a shielded cabin, as known from X-ray tubes in closed environments, e.g. in hospitals, radiation protection is becoming increasingly important.

According to an aspect of the present invention, a mobile X-ray system and a mobile X-ray device with a sensor system is provided. The sensor system detects extrinsic objects, e.g. people and/or objects, that are too close to the X-ray window of the housing of the mobile X-ray device or too close to an X-ray beam of an X-ray source provided by the mobile X-ray device. As a consequence, image acquisition is blocked, if the sensor system signals such proximity of extrinsic objects. Furthermore, operation of the mobile X-ray device is performed only if the X-ray source, the detector and the object to be scanned, a patient for example, are aligned. This assures that the scanning of the object is carried out as desired and an otherwise possible increased or even over dosage for the scanned object is avoided. In some embodiments, the sensor system measures the distance from X-ray source to the detector and the distance of the object, e.g. patient, in front of the detector. By this, it is possible to double check the acquisition parameter with the selected protocol (to avoid over dosage of the patient).

The sensor system itself might comprise a radar sensor (multiple sensors) that monitors the predefined area that would get radiated during exposure, e.g. in front of the X-ray window, at the side and back but also below and above the housing of the mobile X-ray device. As a consequence, the objects around the X-ray source are detected and the distance is measured within few cm precisions. In some embodiments, these objects are tracked by the sensor system.

Other sensor technologies could also be used—however the physical properties of each technology should be suitable for the operation environment. Infrared distance control sensors, time of flight laser distance scanners, ultrasound sensors, the already mentioned radar sensor and camera based sensors could give the required information of the position of the extrinsic object, e.g. a person and/or a scatter object, in relation to the x-ray source. Tracking of multiple extrinsic objects or at least the extrinsic object with the minimum distance is a functionality requirement for the sensor system.

Thus, a more flexible control mechanism for mobile X-ray systems is provided to ensure that an X-ray scan is only performed, if an X-ray source, a detector and an object to be scanned, e.g. a patient, are aligned according to the desired application and no other extrinsic object, e.g. a person, in some embodiments also including the operator, is in a predefined area in the vicinity of the X-ray beam of the X-ray source.

According to the present invention, the mobile X-ray device comprises a housing with an X-ray source arranged therein. The housing might have a shielding and an X-ray window which allows the X-ray beam to reach the object to be scanned. A sensor system is arranged at the mobile X-ray device comprising one or more sensors for the alignment of the X-ray source and the object to be scanned. Furthermore, one or more sensors are provided for detection of at least one extrinsic object in the predefined area in the vicinity of the X-ray beam.

The mobile X-ray device comprises a processor unit. Based on signals received from the sensor system the processor unit is configured to determine the alignment of the X-ray source and the object to be scanned. The processor unit also provides image acquisition for generating an X-ray image of the scanned object. If the signals received by the processor unit from the sensor system indicate at least one extrinsic object within the predefined area or a lack of alignment between the X-ray source and the object to be scanned, the processor unit is configured to activate a blockage signal which blocks image acquisition of the object, to avoid radiation of the object. In particular, a blockage signal is activated which blocks generation of X-ray at the X-ray tube of the mobile X-ray device, the X-ray tube being located in the casing of the mobile X-ray device, to avoid radiation. The X-ray device can be provided with means for giving a warning information like flashing light, sound, display or voice message.

Thus, one key element of the invention is the sensor system that detects extrinsic objects like people or objects that are too close to the X-ray source. Furthermore, an interface is provided for outputting of the generated X-ray image. Also, information like an indication for the reason of blockage can be provided via the interface of the mobile X-ray device. In some embodiments, this could be a display showing the location of the extrinsic object. Furthermore, information like the reason for the blocking of the image acquisition can be indicated by the interface of the mobile X-ray device.

In some embodiments, the mobile X-ray system provides identification means for identifying the object to be scanned, e.g. the patient, as it will be in the proximity of the X-ray source. The same might apply for an operator, if assistance is needed to hold the object or the patient, for example. By providing identification means, it is possible to identify the level of expertise of the operator or to identify previous treatments of a patient. The previous treatments of a patient can comprise data like: skin dose mapping, received radiation dose, exposure time, date of the exposure, number of X-ray acquisitions during the lifetime of a patient and the like.

In some embodiments, such data is calculated during the image acquisition using the parameter settings and functionality of the x-ray system and preferably the additional information from the sensor system. The calculated data is stored in a corresponding data base.

In some embodiments, provisions can be made to cancel the blockage signal provided by the mobile X-ray device, if the operator is classified as an expert operator, e.g. highly skilled hospital personnel, or a profoundly trained operator. This ensures a flexible operation of the system, as skilled operators might need less assistance to fulfill safety requirements as less trained operators.

In some embodiments, a differentiated operation of the mobile X-ray device is provided depending on the operator's expertise. There might be situations when an operator or other person needs to be closer to the patient in the area of higher dose. In these situations, an overruling exception is possible if a certified expert is present and known to the system as an expert. The exception then might be allowed for only one or a limited number of X-ray acquisitions to minimize the integral dose for the additional person close to the patient up to the exception level (from the database). In all cases, the image acquisition is blocked if a person or the operator is directly in front of an X-ray window of the X-ray device or too close to the X-ray source itself.

According to another aspect of the present invention, also a method for image acquisition by use of a mobile X-ray system is provided. An optimized workflow depending on an operator's expertise ensures that all safety requirements for the mobile X-ray system are fulfilled. The mobile X-ray system comprises an X-ray device with a sensor system and a detector. The method comprises the following steps:

determining an alignment of an X-ray source, an object to be scanned and the detector, wherein the X-ray source is provided by the X-ray device;

detecting an absence of at least one extrinsic object in a predefined area in a vicinity of the X-ray beam of the X-ray source;

generating an X-ray image from data received by the detector; outputting the generated X-ray image and/or information;

blocking image acquisition, if the sensor system signals that at least one extrinsic object is detected within the predefined area or lack of alignment between the X-ray source, the detector and the object to be scanned.

In some embodiments, the predefined area is defined as an area extending from the X-ray source and comprising the vicinity of the X-ray beam, the object to be scanned and the detector.

For some embodiments, the predefined area comprises a core area including the X-ray beam, the object to be scanned and the detector, wherein the core area extends therefrom up to a first distance. The predefined area might further comprise a secondary area extending from the core area up to a second distance. Also, a securing area can be provided within the predefined area extending from the secondary area and including the vicinity of the mobile X-ray device.

These areas can be further classified into sections, reflecting the expertise level of an operator of the mobile X-ray device.

In some embodiments, the predefined area comprises the core area, secondary area and securing area if the operator is identified as a low-skilled operator. Thus, the safety regulations can be fulfilled and safe operation, even for low-skilled operators can be provided.

For some embodiments, the image acquisition is continued if the extrinsic object is detected in the core area and/or secondary area and is identified as an expert operator indicating continuation of the image acquisition. Thus, an option is provided for highly experienced personnel, to continue image acquisition even if, an extrinsic object is detected in the area of possible high dosage. This is due to the assumption that there might be situations when an operator or another person has to be closer to the patient in the core area or secondary area which usually provide a higher dose. In these situations, such overruling exception might be possible if e.g. a certified expert is present and known to the system as an expert. The exception then might be allowed for only one or a limited number of x-ray acquisitions to minimize the integral dose for the additional person close to the patient up to the exception level. The dosage levels are taken from a database. In all cases provisions are taken to block the x-ray beam if a person is directly in front of an x-ray window or too close to the X-ray source.

The dose levels in the database might be adjusted according to the local regulations and/or the typical application setting/environments to take care of the environment. E.g. in an ambulance car there might be dedicated areas with radiation shielding which have to be known to the x-ray system.

In some embodiments, the core area, secondary area and/or securing is defined by pre-calculated X-ray radiation dose maps using the actual acquisition settings of the mobile X-ray system would give the result of the actual X-ray radiation dose for the extrinsic object at a certain position and distance to the X-ray source. As soon as the measured dose is higher compared to the allowed value, the X-ray image acquisition is blocked (or stopped in case an extrinsic object moves into the core area during the radiation procedure).

It is possible to perform a calibration procedure by the mobile X-ray system to adjust the pre-calculated X-ray radiation dose setting in an associated database according to usage requirements of the mobile X-ray system.

In some embodiments, outputting information based on the data received by the detector comprises a proposal of possible treatment and/or a diagnosis. Such information might be beneficial especially for the low-skilled operator. Also, assistance for handling of the mobile X-ray system can be provided upon request of the operator.

In some embodiments detecting the at least one extrinsic object comprises tracking the at least one extrinsic object. For the tracking of the extrinsic object multiple sensors of different kind, as mentioned above, can be used.

According to another aspect of the present invention, a computer program element for controlling a mobile X-ray device or mobile X-ray system as mentioned above, which, when being executed by a processing unit, is adapted to perform the described method steps. Furthermore, also a computer readable medium is provided having stored the program element of the described method.

The present invention could be used in mobile healthcare systems like ultra-mobile x-ray systems where x-ray source and x-ray detector are not in a fixed geometry setting but also in interventional x-ray systems and mobile x-ray systems in the hospital. Even in veterinarian x-ray systems and technical inspection systems this technology could improve the safety to avoid over dosage of extrinsic objects, e.g. people, close to the x-ray system.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

Figure 1:
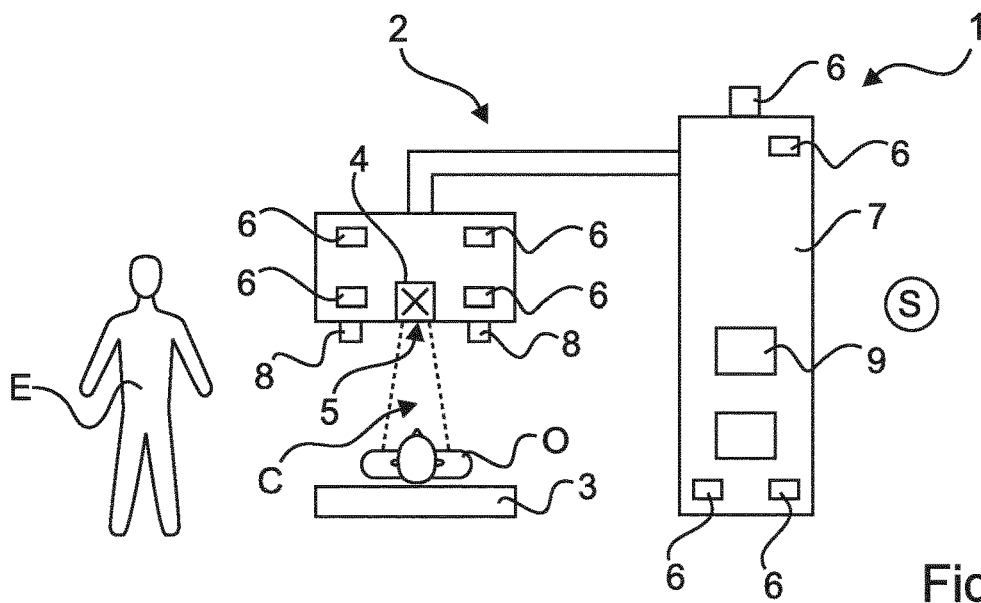
FIG. 1 is a side view of a mobile X-ray system.

FIG. 1 shows schematically a side view of a mobile X-ray system 1. The X-ray system 1 comprises a mobile X-ray device 2 and a detector 3. The mobile X-ray device 2 comprises a housing 4 with an X-ray source X arranged therein. The housing 4 is provided with an X-ray window 5. Multiple sensors 6 are arranged at the housing 4 and at a casing 7 of the mobile X-ray device 2. The arrangement of the sensors 6 are only exemplary, however any suitable location at the X-ray device can be used.

The sensor system 6 might comprise a radar sensor 8 (multiple sensors 8) that monitors a core area C in this embodiment. The core area would get radiated during exposure, e.g. in front of the X-ray window. Other sensors 6 of the same or different kind, e.g. infrared distance control sensors, time of flight laser distance scanners, ultrasound sensors or camera based sensors might also be used for monitoring the core area C or the vicinity of the x-ray beam at the side and back but also below and above the housing of the mobile X-ray device. As a consequence, the object O to be scanned and the extrinsic object E in the vicinity of the X-ray source X are detected and the distance is measured within few cm precisions.

In some embodiments, these extrinsic objects E are not only detected but tracked by the sensor system 6. The required information of the position of the extrinsic object E, e.g. a person and/or a scatter object, in relation to the X-ray source X is thus easily detected. Tracking of multiple extrinsic objects E or at least the extrinsic object E with the minimum distance is a functionality requirement for the sensor system.

The mobile X-ray device 2 comprises a processor unit 9 for processing data received from the sensor system 6 and the detector 3 and to perform the image acquisition. The processor unit 9 activates a blockage signal for the mobile X-ray device which blocks the image acquisition if at least one extrinsic object E is detected within a predefined area in the vicinity of the X-ray beam. In this embodiment the core area C and a securing area S. The processor unit 9 also activates a blockage signal if the sensor system 6 signals a lack of alignment between the X-ray source, the detector 3 and the object O to be scanned.

Figure 2:
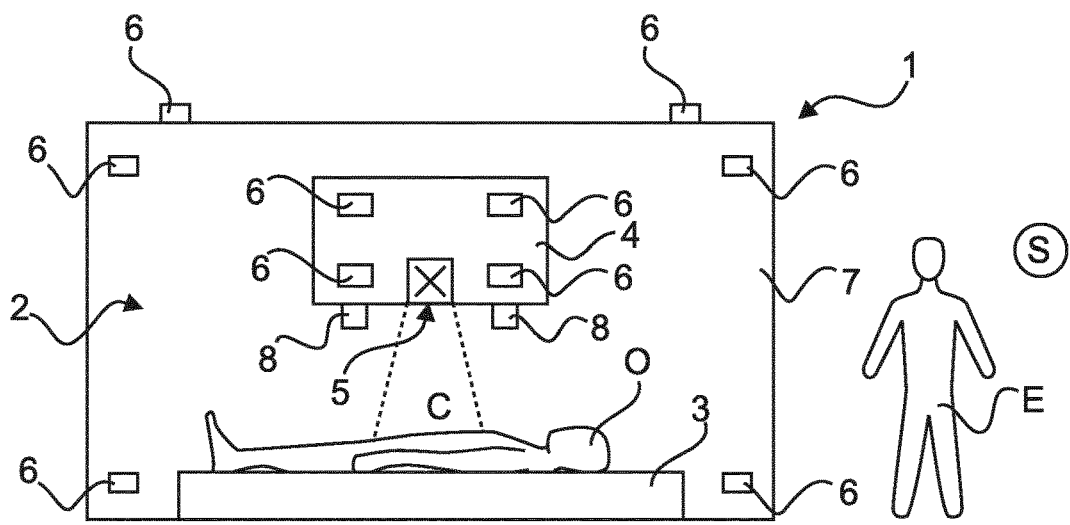
FIG. 2 is a front view of the mobile X-ray system of FIG. 1.

FIG. 2 shows schematically a front view of a mobile X-ray system of FIG. 1. Due to clarity reasons, not all sensors 6 of FIG. 1 are shown (and vice versa in FIG. 1). As in FIG. 1 the core area C would get radiated during exposure. The sensor system 6 comprises multiple sensors 6, 8 arranged at the housing 4 and the casing 7 of the mobile X-ray device 2.

Figure 3:
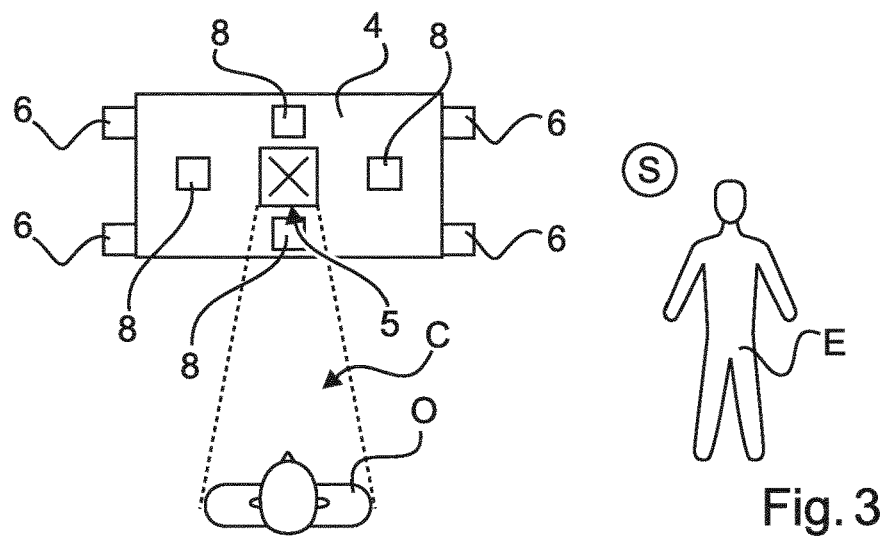
FIG. 3 is a view of an X-ray window of a mobile X-ray device.

FIG. 3 shows a top view X-ray window 5 of a mobile X-ray device 4. The sensors 8 are arranged to easily detect or even track a location or movement of an extrinsic object E in the core area C of the predefined area in the vicinity of the X-ray beam. To facilitate understanding the object O to be scanned and the core area C are also indicated, however the object O and the core area C are located on top of the X-ray window 5 in this perspective. In this figure, the core area C is located above the X-ray window 5. In this embodiment sensors 6 are used for detecting any extrinsic object E outside of area C in a securing area S.

Figure 4:
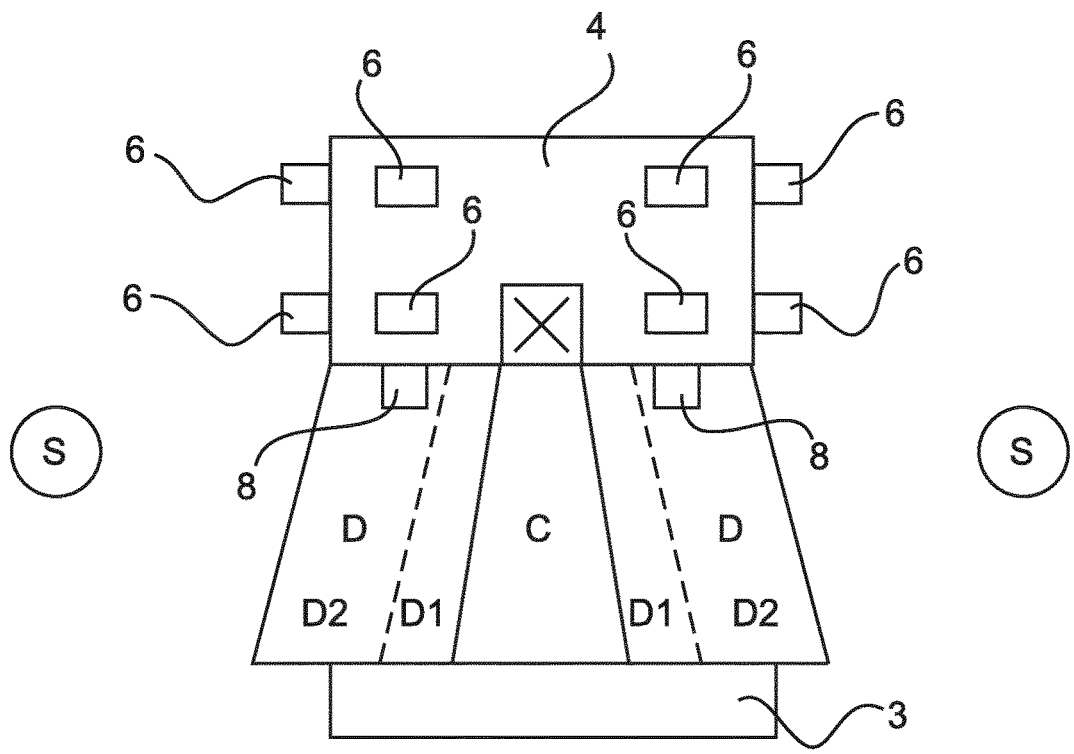
FIG. 4 is a schematic front view of a predefined area in the vicinity of an X-ray beam.

FIG. 4 is a schematic front view of a predefined area in the vicinity of an X-ray beam. A core area C, a secondary area D and a securing area S are shown. Sensors 6, 8 are arranged at a housing 4 of a mobile X-ray device. Due to clarity reasons, the mobile X-ray system is not shown.

A predefined area in the vicinity of the X-ray beam comprises a core area C with the expected highest radiation dose during radiation exposure. The secondary area D abuts the core area C. Depending on the expertise level of an operator of the mobile X-ray system, image acquisition might be continued if an extrinsic object E is detected in the secondary area D. Securing area S is mainly for detecting bystanders/people located too close to the X-ray system without any need.

If applicable or desired the secondary area D can be further divided into secondary sections D1, D2. These sections D1, D2 could be switched on/off depending on the expertise level of the operator of the mobile X-ray system. For a less skilled operator, for example, these subsections D1, D2 could be switched off. In that case, image acquisition is blocked, if an extrinsic object E is detected in the secondary area D. However, if the operator is identified as an operator having a high expertise level, these sections could be switched on automatically, so that in case an extrinsic object E enters the outer section D2, image acquisition continues, however, if the extrinsic object E enters the inner section D1, image acquisition is blocked.

Figure 5:
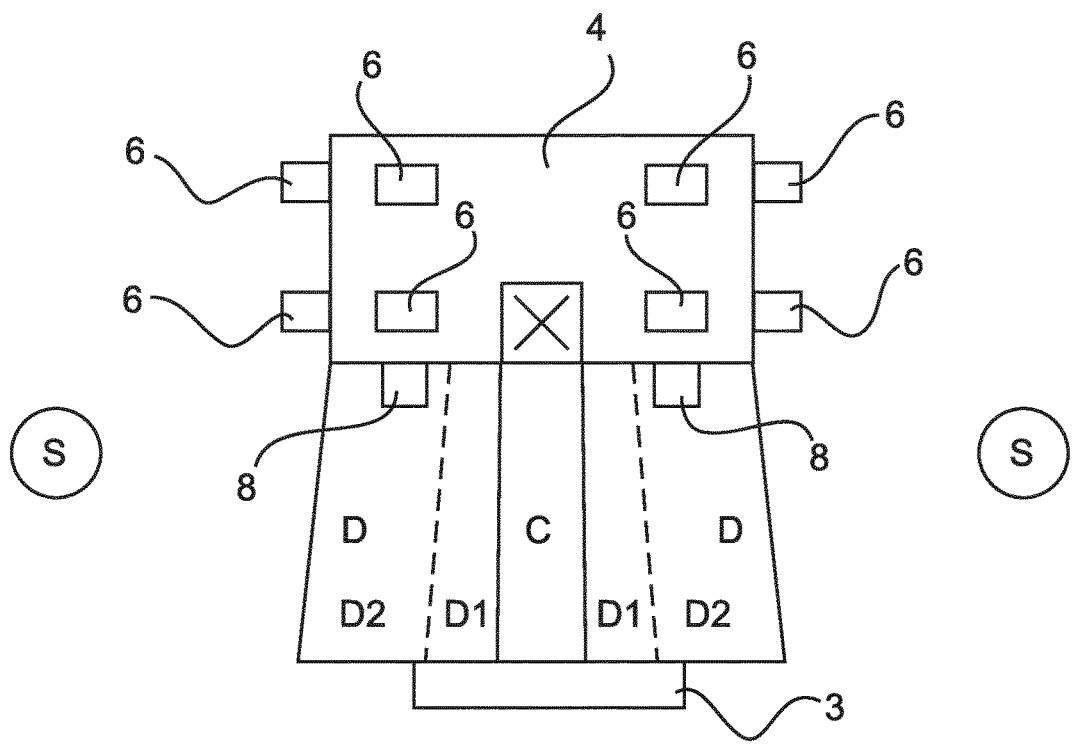
FIG. 5 is a schematic side view of the predefined area of FIG. 5.

FIG. 5 is a schematic side view of the predefined area of FIG. 5 and shown only to explain the 360° monitoring of the X-ray mobile system.

Figure 6:
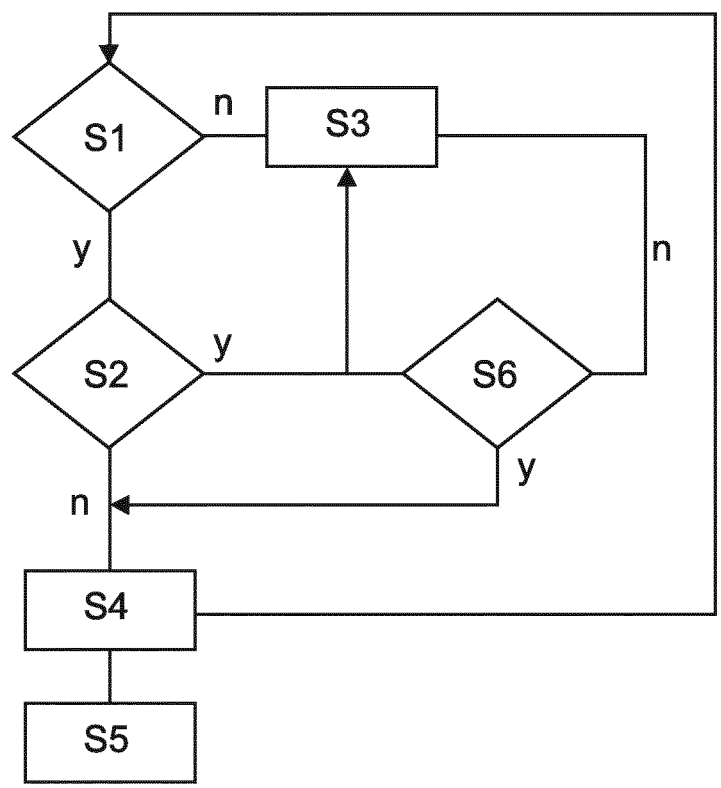
FIG. 6 depicts a first basic flow chart.

FIG. 6 depicts a first basic flow chart. In a step S1 the alignment of the X-ray source X provided in the housing of the mobile X-ray device 4, an object O to be scanned and the detector 3 is performed. In case the alignment is correct detection of an absence of at least one extrinsic object E in a predefined area in the vicinity of the beam is performed at step S2. Otherwise the image acquisition is blocked at step S3 until the extrinsic object E is removed. Also, if an extrinsic object E is detected at step S2 the image acquisition is blocked at step S3.

If the X-ray source X, the detector 3 and the object O to be scanned are aligned and no extrinsic object E is detected, image acquisition is performed at step S4 and an X-ray image is generated and outputting of the X-ray image and/or additional information is performed at step S5.

Optionally, an identification procedure (step S6) for the operator is performed after an extrinsic object E is detected at step S2. If the operator is an expert operator image acquisition might continue at step S4 based on his/her level of expertise. In case the operator is a low-skilled operator image acquisition is blocked at step S3.

During exposure of an object to be scanned, the sensor system signals any mis-alignment or detected extrinsic object and image acquisition is blocked.

Figure 7:
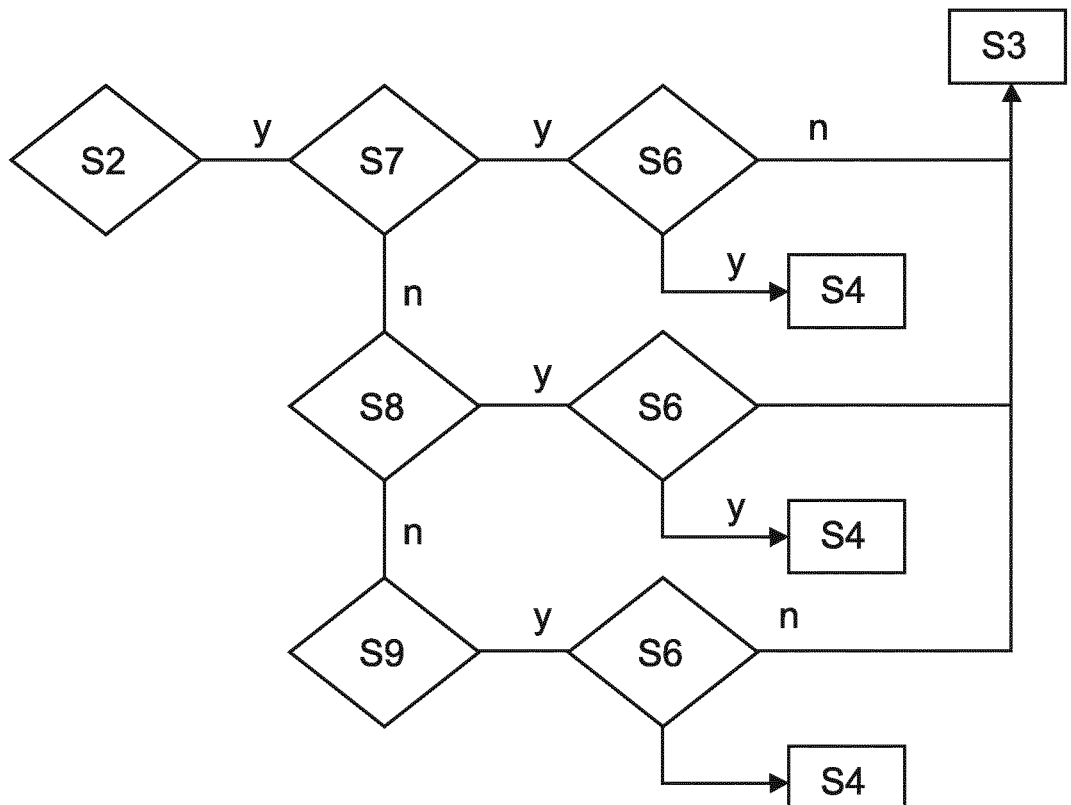
FIG. 7 depicts a second basic flow chart.

FIG. 7 depicts a second basic flow chart which could be used after step S2 in the flowchart of FIG. 6. If the signals provided by the sensor system 6 of the mobile X-ray device indicate an extrinsic object E in the vicinity of the X-ray beam, those signals are analyzed to identify if the extrinsic object E is in a core area C (step S7). If a core area C is identified, an identification procedure at step S6 is performed. If no expert operator is identified image acquisition is blocked (step S3). If the operator is an expert, image acquisition might continue after indication of the operator (step S4).

If the extrinsic object E is detected outside the core area C, the signals are analyzed to identify the extrinsic object in a secondary area D (step S8). If a secondary area D is identified, an identification procedure at step S6 is performed. If no expert operator is identified image acquisition is blocked (step S3). If the operator is an expert, image acquisition might continue after indication of the operator (step S4).

If the extrinsic object E is detected outside the secondary area, the signals are analyzed to identify the extrinsic object in a securing area S (step S9). If a securing area S is identified, an identification procedure at step S6 is performed. If no expert operator is identified image acquisition is blocked (step S3). If the operator is an expert, image acquisition might continue after indication of the operator (step S4).

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section. A computer program may be stored and/or distributed on a suitable medium, such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated, and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:
1. A mobile X-ray device comprising:
a housing with an X-ray source;
a sensor system comprising at least one sensor for aligning the X-ray source with an object to be scanned and detecting at least one extrinsic object in a predefined area near an X-ray beam of the X-ray source;
a processor configured to
determine whether the X-ray source and the object to be scanned are aligned based on signals received from the sensor system;
perform an image acquisition for generating an X-ray image; and
activate a blockage signal based on the signals received from the sensor system; and
an interface for outputting the generated X-ray image;
wherein the image acquisition is not performed when the signals indicate that:
the at least one extrinsic object is detected within the predefined area; or the X-ray source and the object to be scanned are not aligned.

2. A mobile X-ray system, comprising:
an X-ray detector; and
a mobile X-ray device that includes:
   a housing with an X-ray source;
   a sensor system comprising at least one sensor for aligning the X-ray source with an object to be scanned and detecting at least one extrinsic object in a predefined area near an X-ray beam of the X-ray source;
   a processor configured to
     determine whether the X-ray source and the object to be scanned are aligned based on signals received from the sensor system;
     perform an image acquisition for generating an X-ray image; and
     activate a blockage signal based on the signals received from the sensor system; and
   an interface for outputting the generated X-ray image;
   wherein the image acquisition is not performed when:
     the at least one extrinsic object is detected within the predefined area;
     the X-ray source and the object to be scanned are not aligned; or
     the X-ray source, the X-ray detector and the object to be scanned are not aligned.

3. The system according to claim 2, wherein an operator and/or the object to be scanned is identified.

4. The system according to claim 3, wherein the blockage signal is cancelled when the operator is identified as an expert.

5. A method for image processing by a mobile X-ray system that comprises an X-ray source, a sensor system and an X-ray detector, the method comprising:
   determining, by the sensor system, whether the X-ray source, an object to be scanned and the X-ray detector are aligned;
   detecting, by the sensor system, at least one extrinsic object in a predefined area near an X-ray beam of the X-ray source;
   performing an image acquisition for generating an X-ray image;
   outputting the generated X-ray image; and
   blocking the image acquisition when
     the at least one extrinsic object is detected within the predefined area; or
     the X-ray source, the object to be scanned and the X-ray detector are not aligned.

6. The method according to claim 5, wherein the predefined area is an area extending from the X-ray source and comprises a vicinity of the X-ray beam, the object to be scanned and the X-ray detector.

7. The method to claim 5, wherein the predefined area comprises:
   a core area including the X-ray beam, the object to be scanned and the X-ray detector, wherein the core area extends a first predetermined distance;
   a secondary area extending from the core to a second predetermined distance; or
   a secure area extending from the secondary area and including the vicinity of a mobile X-ray device.

8. The method according to claim 7, wherein the predefined area comprises the core area, the secondary area and the secure area when an operator is identified as low-skilled.

9. The method according to claim 7, wherein the image acquisition is continued when the extrinsic object is detected in the core area or the secondary area, and an operator is identified as an expert operator.

10. The method according to claim 7, wherein the core area, the secondary area or the secure area is defined by comparing a pre-calculated X-ray radiation dose against an actual X-ray radiation dose at a position of the detected extrinsic object.

11. The method according to claim 10, further comprising performing a calibration by the mobile X-ray system to adjust the pre-calculated X-ray radiation dose in a database according to usage requirements of the mobile X-ray system.

12. The method according to claim 5, further comprising outputting information based on data received by the X-ray detector, the information comprising a possible treatment or a diagnosis.

13. The method according to claim 5, further comprising tracking the at least one extrinsic object.

14. A non-transitory computer-readable medium having one or more executable instructions, when executed by a processor, cause the processor to perform a method for image processing by a mobile X-ray system that comprises an X-ray source, a sensor system and an X-ray detector, the method comprising:
   determining, by the sensor system, whether the X-ray source, an object to be scanned and the X-ray detector are aligned;
   detecting, by the sensor system, at least one extrinsic object in a predefined area near an X-ray beam of the X-ray source;
   performing an image acquisition for generating an X-ray image;
   outputting the generated X-ray image; and
   blocking the image acquisition when
     the at least one extrinsic object is detected within the predefined area; or
     the X-ray source, the object to be scanned and the X-ray detector are not aligned.

* * * * *